United States Patent [19]

Fields

[11] 4,174,447

[45] Nov. 13, 1979

[54] PROCESS FOR DIMERIZATION, ARYLATION AND TRIFLUOROMETHYLATION OF AROMATIC AND HETEROCYCLIC COMPOUNDS

[75] Inventor: Ellis K. Fields, River Forest, Ill.

[73] Assignee: Standard Oil Company (Indiana), Chicago, Ill.

[21] Appl. No.: 553,093

[22] Filed: Feb. 26, 1975

[51] Int. Cl.$^2$ .......................................... C07D 401/04
[52] U.S. Cl. ..................... 546/109; 549/43; 549/49; 549/59; 549/29; 548/152; 260/343.21; 260/346.3; 260/346.7; 260/414; 260/347.91; 260/430; 260/465 H; 260/465 R; 260/346.22; 260/343.44; 560/76; 546/140; 546/167; 546/260; 548/328; 204/157.1 R; 204/162 R; 548/202; 549/83; 585/425; 585/427
[58] Field of Search .......... 260/283 P, 283 A, 283 R, 260/283 D, 288 CE, 283 B, 2.5 R, 78.4 R, 430, 414, 290 R, 296 D, 670 R, 668 F; 252/476

[56] References Cited

U.S. PATENT DOCUMENTS

| | | | |
|---|---|---|---|
| 2,446,132 | 7/1948 | Evans | 252/476 |
| 2,773,844 | 12/1956 | Carlson | 252/476 |
| 3,144,416 | 8/1964 | Hosada | 252/476 |
| 3,775,352 | 11/1973 | Leonard, Jr. | 260/2.5 R |
| 3,779,952 | 12/1973 | Leonard, Jr. | 260/2.5 R |
| 3,943,069 | 3/1976 | Antonelli | 252/476 |
| 4,065,442 | 12/1977 | Fields et al. | 252/476 |

*Primary Examiner*—Donald G. Daus
*Assistant Examiner*—M. Lee
*Attorney, Agent, or Firm*—William C. Clarke; Arthur G. Gikes; William T. McClain

[57] ABSTRACT

A decarboxylation process for coupling aromatic compounds wherein cyclic hydrocarbons and heterocyclic compounds having at least one labile ring hydrogen are reacted with the mono silver salts of aromatic carboxylic acids, or mono silver salts of unsaturated compounds such as $\alpha,\beta$-ethylenically unsaturated acid compounds, or silver trifluoroacetate, or the mono silver salts are reacted with themselves, by heating to temperatures of 100° to 500° C. at pressures of 0.1 to 10 atmospheres, or by irradiating the reactants with ultraviolet light of 200 to 400 nanometers at temperatures of $-30°$ to 150° C. The resulting dimers, trimers, polysubstituted polyphenyls, polyheterocyclics and trifluoromethylated aromatics are useful as heat transfer media, as intermediates for high molecular weight polymers, pesticides and petroleum additives, and as scintillation counters.

10 Claims, No Drawings

PROCESS FOR DIMERIZATION, ARYLATION AND TRIFLUOROMETHYLATION OF AROMATIC AND HETEROCYCLIC COMPOUNDS

BACKGROUND OF THE INVENTION

The field of this invention relates to a economical, safe, on-the-shelf decarboxylation process using mono silver salts for arylating and dimerizing aromatic compounds, and for coupling polysubstituted cyclic hydrocarbons and heterocyclics. The process also can be used to trifluoromethylate aromatic compounds.

Usually a decarboxylation reaction results in the generation of carbon dioxide and the concurrent replacement with hydrogen on the molecule. For example, the decarboxylation or benzoic acid yields benzene and carbon dioxide. Pyridine carboxylic acid goes to pyridine and carbon dioxide without any linkage occurring between two pyridine radicals. The presence of other carboxylic acid salts such as a sodium carboxylate of an aromatic acid will merely aid in the decarboxylation reaction at best and char to yield an ill-defined residue. The decarboxylation reaction products of this invention, on the contrary, are silver, carbon dioxide, and the coupled organic radicals of the silver carboxylates in the form of dimers, trimers, and multiples thereof, as well as coupled organic radicals of the other reactants present in multiple combinations. Surprisingly, mono silver salts of aromatic carboxylic acids form dimers, trimers, etc, when energy is applied instead of polymerizing to high polymers as do the di- and poly silver salts of polycarboxylic acids, as disclosed in copending U.S. application, Ser. No. 519,640 of Fields, Zimmerschied and Palmer.

In general, arylation or the coupling of aryl components by the formation of a bond between two aromatic carbons, either of aromatic or heteroaromatic compounds, is not by means of a decarboxylation reaction. The creation of such a bond, which almost invariably eliminates a hydrogen atom and has been defined as essentially a substitution reaction, is usually a homolytic aromatic substitution reaction. Among the reactions employed to achieve a desired homolytic substitution have been reactions involving diazo-, azo-, and related compounds, reactions involving peroxides and other sources of aroyloxy-radicals, photochemical reactions, and miscellaneous reactions such as use of certain Grignard reagents with specific reactants.

Many coupling reactions involving diazo-, azo-, and related compounds have been reported but frequently the reactions are specific to the preparation of certain compounds or these compounds decompose with explosive force unless precautions are taken. A biaryl can be formed in yields of 5 to 40% based upon the amine using an aqueous solution of a sodium azide with a neutral aromatic liquid stirred in the cold. Other examples are the use of a diazonium salt in aqueous acetone in the presence of cupric chloride to prepare biaryl derivatives, the preparation of nitrobiphenyls from a diazotised nitroaniline and benzene with aqueous sodium acetate or aqueous sodium hydroxide, the preparation of biphenyl when aniline is boiled under reflux with butyl and pentyl nitrite and benzene, and in the use of diazonium tetrafluoroborates in the presence of pyridine to form aryl radicals. A general method for homolytic arylation in a homogeneous medium is in the reactions of acylarylnitrosamines, which is exemplified by the decomposition of nitrosoacetanilide in benzene to give the biphenyl. Analogous reactions are possible with toluene, chlorobenzene, benzaldehyde and nitrobenzene. Homolysis of a diazophosphate to give aryl radicals which then can react with an aromatic solvent is another example.

Coupling reactions involving peroxides and other sources of aroyloxy radicals to arylate aromatic compounds are also well-known. But again these reactants have been reported frequently as decomposing with explosive force unless precautions are taken, or the reactions are specific to the preparation of certain compounds. Diaroyl peroxides react in aromatic solvents to yield the aryl radical, and result in the arylation of the aromatic solvent. Lead tetrabenzoate decomposes in aromatic solvents to give biaryls but because of the relative weight of lead, the process is highly uneconomic as compared with the disclosed invention. Phenyl iodosobenzoate upon decomposition gives the phenyl radical for the phenylation of the aromatic solvent.

Photochemical reactions are known to be sources of aryl radicals, in particuiarly the photolysis of organometallic compounds and aryl halides, p-Terphenyl, as an example, can be obtained from photolysis of 4-iodobiphenyl and benzene. 2,4,6-Tri-iodophenol plus benzene is known to give 2,4,6-triphenylphenol, for another example. Photochemical reactions however, often suffer from the handicaps of being specific to the preparation of certain compounds and whether a halide or an organo-metallic compound is available as a reactant. Further, the UV light that brings about the reaction causes additional reactions of the primary products.

Reactions for introducing fluorine into aromatic compounds are also well-known, such as the often-used Swarts reaction which utilizes antimony trifluoride. A chlorine atom in the molecule is replaced by a fluorine atom. The process is hence a two-step process, requiring first the introduction of chlorine atoms. The Swarts reaction can also involve problems of control, as many aromatic chlorides react very rapidly with antimony fluoride.

SUMMARY OF THE INVENTION

The novel process is a decarboxylation method using mono silver salts for arylating and dimerizing aromatic compounds, for synthesizing substituted styrenes and diarylbutadienes, for coupling polysubstituted cyclic hydrocarbons and heterocyclics, and for trifluoromethylating aromatics by heating the reactants or by irradiating them with ultra-violet light according to the following general equations,

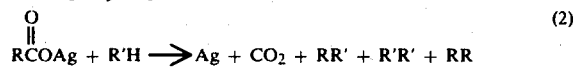

where R and R' are monovalent radicals, where (R minus H) is a divalent radical formed by removal of a hydrogen atom from the monovalent radical R, and where n is an integer from one to seven. R and R' can be aromatic radicals such as phenyl, biphenyl, naphthyl, phenanthryl or anthranyl, or heterocyclic radicals of aromatic character with energy stabilization in excess of open chain and strictly cyclic analogues due to resonance. Examples are thienyl, pyridyl, benzothienyl, thienobenzenyl, quinolyl, isoquinolyl, dibenzothienyl and phenanthridyl radicals. R and R' can also contain substituents such as fluorine, chlorine, bromine, iodine, phosphorus, hydroxy, alkoxy, nitro, carbomethoxy, alkyl and cyano.

can be the mono silver salt of any unsaturated aliphatic acid compound but an α,β-ethylenically unsaturated acid compound is preferred. It can be substituted with halogen, alkoyl, alkylthio or carbalkoxyl radicals. R can also be a trifluoromethyl group and R' can be an aromatic group of one to ten benzene rings, linked together or fused. These rings can be substituted by halogens, nitro, cyano, carboalkoxy, alkoxy, alkyl, acyl and aroyl groups. The polysubstituted polyphenyls and polyheterocyclics are useful as intermediates for polymers, pesticides and petroleum additives, and as scintillation counters. The biphenyls are useful as heat transfer media.

DETAILED DESCRIPTION OF THE INVENTION

It has been found in accordance with this invention that aromatic and heterocyclic compounds can be arylated and trifluoromethylated in a convenient manner by thermally decarboxylating mono silver carboxylates or, alternatively, by the decarboxylation by ultra-violet light of mono silver carboxylates solubilized by tertiary ring nitrogen compounds and triaryl phosphines or in benzene.

For purposes of this invention the terms "mono silver carboxylates" and "mono silver salts" are defined as those silver salts wherein the hydrogen of a single carboxyl radical attached to an aliphatic or aromatic moiety, including a heterocyclic moiety, and combinations thereof, is replaced by a silver metal ion. It is essential for purposes of this invention that only one silver salt group be present per molecule, irrespective of whether or not the molecule contains one or more acyl groups. If a double or poly silver salt of a polycarboxylic acid is present, upon the application of energy the compounds polymerize to high polymers rather than dimerizing, trimerizing, etc. as do the mono salts. The latter is the subject of copending U.S. application, Ser. No. 519,640 of Fields, Zimmerschied and Palmer. Only the mono silver salts decarboxylate to yield carbon dioxide and the recoverable coupled organic radicals in the form of dimers, trimers, and multiples thereof, as well as coupled organic radicals of the other reactants present in multiple combinations. It is also essential for purposes of this invention that at least one carbon to carbon double bond be present in the aliphatic silver salts. The unsaturated aliphatic acid compound can be of any type but the α,β-ethylenically unsaturated acid compound is preferred.

"Aryl radical" is defined, for purposes of this invention, as a monovalent radical derived from an aromatic hydrocarbon. In terms of this invention, the term "aryl compounds" is defined as including aromatic compounds characterized by at least one benzene ring, i.e., either the six carbon ring of benzene or the condensed six-carbon rings of the other aromatic derivatives such as naphthalene, phenanthrene, anthracene, etc. "Aryl carboxylic acids" are defined as aromatic compounds having at least one free valence of the aryl group attached directly to the carboxylic acid group. The term "heterocyclic compound" is defined as a compound containing a cyclic or ring structure in which one or more of the atoms in the ring is an element other than carbon and can be oxygen, nitrogen and/or sulfur. The term "ring compound" is defined as an organic compound whose structure is characterized by a closed ring. It is also termed a cyclic compound. Ring or cyclic compounds can be alicyclic, aromatic (or arene) and heterocyclic.

My process for arylating and trifluoromethylating compounds avoids the disadvantages of alternative coupling methods. These involve reactions of diazo-, azo-, and related compounds, and of peroxides and other sources of aroyloxy-radicals. These reactants can decompose explosively or are specific to the preparation of certain compounds. The process of this invention provides an economical, safe source of aryl and trifluoromethyl radicals. Further, the process has the additional advantage that the silver of the silver carboxylate can be recovered. These mono silver salts are safe, not subject to sudden decomposition. The reactants can be shelf items ready-for-use as needed. The utility of the novel process is well demonstrated inasmuch as well-known compounds with known and demonstrated utility result from the process.

The versatility of the novel decarboxylation process indeed adds to its utility. The novel process may be represented by the following general equation

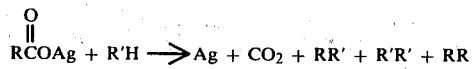

where R and R' can be monovalent unsaturated aliphatic, aryl, heterocyclic radicals and mixtures thereof. R and R' can be unsaturated aliphatics having one, two, and three carbon to carbon double bonds. R and R' can be aromatic radicals such as phenyl, biphenyl, naphthyl, phenanthryl or anthranyl, or heterocyclic radicals of aromatic character such as thienyl, pyridyl, benzothienyl, thienobenzenyl, quinolyl, isoquinolyl, dibenzothienyl and phenanthridyl. R'H— should have at least one labile ring hydrogen. Additionally, R and R' can contain substituents such as fluorine, chlorine, bromine, iodine, phosphorus, hydroxy, alkoxy, nitro, carbomethoxy and cyano.

can be the mono silver salt of any unsaturated aliphatic compound but an α,β-ethylenically unsaturated acid compound is preferred.

can be substituted with halogen, alkoyl, alkylthio, or carboalkoxyl radicals. R can be a trifluoromethyl group and R' can be an aromatic group of one to ten benzene rings, linked together or fused. These rings can be substituted by halogens, nitro, cyano, carboalkoxy, alkoxy, alkyl, acyl and aroyl groups.

Examples of the mono silver salts which can be so reacted, among others, are silver acrylate; silver sorbate; silver cinnamate; silver 1,3,5-heptatrienoate; silver benzoate; silver 4-biphenylcarboxylate; silver 1-phenanthrene carboxylate; silver 2-phenanthrene carboxylate; silver 9-phenanthrene carboxylate; silver 1-anthracene carboxylate; silver 2-anthracene carboxylate; silver 9-anthracene carboxylate; silver 2-thiophene carboxylate; silver 2-pyridinecarboxylate; silver 4-quinoline carboxylate; silver 1-isoquinoline carboxylate; silver 3-dibenzothiophenecarboxylate; silver 3-dibenzofurancarboxylate; silver m- and p-fluorobenzoates; silver m- and p-chlorobenzoates; silver m- and p-iodobenzoates; silver m- and p-bromobenzoates; silver m- and p-diphenylphosphinobenzoates; silver m- and p-diphenyloxophosphinobenzoates; silver m- and p-diphenylthiophosphinobenzoates; silver 3-, 4-, 5- and 6-diphenylphosphino-1-naphthoates; silver 3-, 4-, 5-, and 6-diphenylphosphino-2-naphthoates; silver m- and p-hydroxy benzoates; silver m- and p-methoxy benzoates; silver m- and p-ethoxybenzoates; silver m- and p-methylthiobenzoates; silver m- and p-ethylthiobenzoates; silver m- and p-dimethylaminobenzoates; silver m- and p-diethylaminobenzoates; silver m- and p-nitrobenzoates. Examples of the aromatic and heterocyclic compounds which can be reacted with these silver salts are, among others; fluorobenzene; o-, m- and p-difluorobenzenes; o-, m- p- and di-bromobenzenes; o-, m-, p- and di-chlorobenzenes; o-, m-, p- and di-iodobenzenes; pentafluorobenzene; pentabromobenzene; pentachlorobenzene; pentaiodobenzene; 1,2,3-trifluorobenzene; 1,2,4-trifluorobenzene; 1,3,5-trifluorobenzene; 1,2,3-trichlorobenzene; 1,2,4,5-tetrafluorobenzene; 1,2,4-trichlorobenzene; 1,3,5-trichlorobenzene; 1,2,3,4-tetrachlorobenzene; 1,2,3,5-tetrachlorobenzene; 1,2,4,5-tetrachlorobenzene; as well as the tribromo and tri-iodobenzene isomers; the tetrabromo and tetraiodobenzene isomers; triphenylphosphine; triphenylphosphine oxide; triphenylphosphine sulfide; diphenylnaphthylphosphine; diphenylnaphthyl oxide; diphenylnaphthyl sulfide; phenyldinaphthylphosphine; phenyldinaphthylphosphine oxide; phenyldinaphthylphosphine sulfide; nitrobenzene; m- and p-dinitrobenzenes; anisole; phenetole; m- and p-dimethoxybenzenes; m- and p-diethoxybenzenes; thioanisole; thiophenetole; m- and p-dimethylthiobenzenes; m- and p-diethylthiobenzenes; N,N-dimethylaniline; N,N-diethylaniline; triphenylamine; methyl benzoate; ethyl benzoate; dimethyl terephthalate; dimethyl isophthalate; dimethyl phthalate; trimethyl trimellitate; trimethyl trimesate. Additionally,

in the absence of R'H, can react by decomposition, thus adding to the versatility of the novel process, according to the following general equation:

where R is a monovalent radical, where (R minus H) is a divalent radical formed by removal of a hydrogen atom from the monovalent radical R, where R is an aromatic, heterocyclic or unsaturated aliphatic radical containing three to 26 carbon atoms, having one to three carbon to carbon double bonds, and where n is an integer from one to seven.

It is understood that the above equations are not quantitative but merely represent qualitatively the general aspects of the novel process.

If it is desired to arylate and dimerize aromatic compounds and heterocyclic compounds of aromatic nature, the decarboxylation reaction is run by heating together the mono silver salt of the carboxylic acid and the other reagent R'H in mole ratios of 1:20 to 10:1 at 100°–500° C. for one minute to 24 hours. Preferred conditions are mole ratios of 1:5 to 2:1 at 200°–400° C. for 5–60 minutes. If irradiation is used, the solution of silver salt in the reagent is irradiated by ultraviolet light of 200–400 nanometers preferably while the solutions are being rotated mechanically in Vycor or quartz flasks, at $-30°$ to $100°$ C. for one to 100 hours. As is well-known, Vycor or quartz must be used to permit the ultraviolet light to penetrate the flasks.

The versatility and usefulness of the novel decarboxylation process is demonstrated by its suitability for synthesizing substituted styrenes and 1,4-diarylbutadienes. In the synthesis of substituted styrenes and 1,4-diarylbutadienes, the process consists of heating silver salts of $\alpha,\beta$-ethylenically unsaturated acid compounds such as cinnamic and substituted cinnamic acids at 225°–400° C. for 1–120 minutes, preferably under an inert gas such as nitrogen or helium, at pressures of 0.1 to 10 atmospheres. Preferred conditions are 260°–330° C. for 5–10 minutes at one atmosphere pressure. Examples of mono silver salts of cinnamic and substituted cinnamic acids which can be reacted by this process are, among others, silver cinnamate; silver o-, m, and p-monochlorocinnamates; silver 2,6- and 3,4-dichlorocinnamate; silver 2,4-dihydroxycinnamate; silver 3,5-dimethoxy-4-hydroxy cinnamate.

If it is desired to arylate and dimerize aromatic compounds such as the mono silver salts of organic carboxylic acids by the novel process, the reaction is run by heating the silver salts to controlled temperatures of 150°–500° C. These salts decarboxylate at these temperatures to form dimers RR, as well as trimers and higher polymers. The general formula for the product is $R(R \text{ minus } H)_n R$ where R is a monovalent aromatic heterocyclic or unsaturated aliphatic radical containing three to 26 carbon atoms, and may contain substituents such as halogen, nitro, cyano, alkoxy, carboxy, carbomethoxy, dicarboxylic acid anhydride, SR, $SO_2R$ and phosphonyl groups. (R minus H) is a divalent radical formed by removal of a hydrogen atom from the monovalent radical R. The n is an integer from one to seven.

Examples of the mono silver salt compounds which can be so reacted, among others, are silver benzoate; silver p-toluate; silver p-cyanobenzoate; silver monomethyl terephthalate; silver trimellitate anhydride; silver m-toluate; silver 4-biphenylcarboxylate; silver p-hydroxybenzoate; silver thiophene-2-carboxylate; silver nicotinate; silver isonicotinate; silver phenylacetate; silver p-nitrobenzoate; silver 2-naphthoate; silver adamantane-carboxylate; silver octoate; silver acrylate; silver undecylenate; silver oleate; silver monomethyladipate; silver picolinate; silver o-fluorobenzoate; silver m-fluorobenzoate; silver p-fluorobenzoate; silver pentafluorobenzoate; silver erucate; silver brassidate; silver 3-chloroacrylate; silver 3-fluoroacrylate; silver 3-bromoacrylate; silver 3-chlorocrotonate; silver 3-bromocrotonate; silver 4-fluorocrotonate; silver salts of mono-fluoro, mono-chloro, and monobromo substituted mono-carboxylic acids containing from 6 to 18 carbon atoms with at least one carbon to carbon double bond such as silver 9-fluorooleate, silver 9-chlorooleate, silver 9-bromooleate, silver 10-fluoroundecylenate; silver 11-nitroundecylenate; silver 3-cyanoacrylate; silver 4-methoxy crotonate; silver 4-ethoxy crotonate; mono silver maleate; mono silver fumarate; silver monocarbomethoxyacrylate; silver monocarboethoxy acrylate; mono silver salt of carboxy maleic anhydride; silver 3-methylthioacrylate; silver 3-ethylthioacrylate; silver 3-methylsulfonylacrylate; silver 3-P,P-dimethyl phosphonylacrylate; silver 11,12-tetracosenoate; silver 12,13-hexacosenoate; silver linoleonate; silver sorbate; silver 1,3,5-heptatrieneoate.

The reactions can be run in a variety of suitable reactors such as a sublimation apparatus, at pressures of 0.001 to 1000 Torr, for periods of one second to one hour. Longer periods at higher temperatures will serve to sublime out volatile products and will simplify recovery. The cooled mixture of silver and product is extracted with a solvent such as ether, acetone or benzene, filtered and distilled to recover the product. Alternatively, the silver salt of this invention can be decarboxylated by heating in a combustion tube of Pyrex, Vycor, quartz or stainless steel, contained in a furnace under an inert gas such as nitrogen or helium. The volatile products are collected in a receiver cooled in ice, dry ice-acetone, or liquid nitrogen. For large-scale industrial use, a hopper feeds the solid silver carboxylate salt on to a continuous moving belt which enters a furnace at 200°–450° C. where the silver salt is decarboxylated and the volatile material is removed under a stream of nitrogen and caught in a cooled receiver. The belt, after leaving the furnace, drops the silver metal into a chute and receiver where the recovered silver is collected for conversion into more silver carboxylate salt.

Additionally, the novel decarboxylation process is suitable for introducing trifluoromethyl groups, $CF_3$, into aromatic compounds in one step, using the silver salt of trifluoroacetic acid, $CF_3COOAg$, again according to the general formula $$CF_3COOAg + R'H \rightarrow R'CF_3 + CO_2 + Ag$$

where R'H can be a ring compound, either aromatic or heterocyclic, or mixtures thereof. R'H can be an aromatic compound of one to ten benzene rings, linked together or fused. These rings can be substituted by halogens, nitro, cyano, carboalkoxy, alkoxy, alkyl, acyl, and aroyl groups. Examples of compounds wich can be trifluoromethylated by this novel process are: benzene, fluorobenzene, chlorobenzene, bromobenzene, nitrobenzene, benzonitrile, methyl benzoate, anisole, toluene, xylenes, acetophenone, benzophenone, biphenyl, terphenyls, quaterphenyls, naphthalene, anthracene, phenanthrene, pyrene, benzpyrene, coronene, pyridine, quinoline, phenanthridine, thiophene, benzothiophene, dibenzothiophene, furan, benzofuran, dibenzofuran, thiazole and benzothiazole, benzimidazole, benzoylbiphenyl, benzoylpyridine and benzoyl phenylpyridine.

In the introduction of trifluoromethyl groups, $CF_3$, into aromatic compounds in one step, the following adaptation of the general method is used. Solutions of silver trifluoroacetate in aromatic compounds, 1% to 50% by weight, are heated at 250°–300° C. for one to 200 minutes. Preferred conditions are: silver trifluoroacetate 3–20% by weight, 260°–280° C. for 5 to 20 minutes. The trifluoromethylated product is separated from the metallic silver in a suitable manner, as by solubilizing in acetone, ether or other solvent, followed by filtration and distillation. If irradiation is used, the solution of silver trifluoroacetate in the aromatic compound is irradiated by ultraviolet light of 200 to 400 nanometers, preferably while the solutions are being rotated mechanically in Vycor or quartz flasks, at −25° to 150° C. for one to 150 hours.

In order to facilitate a clear understanding of the invention, i.e., the novel decarboxylation process using mono silver salts for the arylation, dimerization, and trifluoromethylation of aromatic and heterocyclic compounds, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

Examples I through VII illustrate the arylation and dimerization of aromatic and heterocyclic compounds, Examples VIII–XIV the synthesis of styrenes and 1,4-diaryl butadienes, Examples XV–XXXI the process for dimerization of organic molecules, and Examples XXXII through XXXVI the trifluoromethylation of aromatic compounds.

EXAMPLE I 11.45 Grams (0.05 mole) of silver benzoate were dissolved in 11.8 ml. (0.1 mole) of quinoline by being heated slowly in a combustion tube. All solids were in solution at 110° C. The solution was heated to 190° C., kept there for 40 minutes, then cooled. The benzene-soluble materials were extracted with 100 ml. of benzene and filtered. The filtrate was distilled at 100° C. and 0.2 mm Hg to remove the benzene and to recover 7.3 grams of quinoline. The 2.7 gram residue analyzed 88% biquinolyl and 12% phenylquinoline. The benzene-insoluble portion consisted of 5.3 grams of silver metal. Analysis was by directly-coupled gas chromatography - mass spectrometry.

EXAMPLE II

A solution made by heating 11.45 grams (0.05 mole) of silver benzoate and 12 ml. (0.15 mole) of pyridine at 100° C., was heated slowly to a pot temperature of 200° C. and kept there for 10 minutes. Pyridine, 9 ml, was distilled off. The cooled residue was extracted with two 100 ml. portions of ether which was then filtered. The ether solution was heated to dryness on a steam bath to remove the ether. The 2.0 gram residue analyzed 16.9% phenylpyridine, 3.1% bi-pyridyl, and 80.0% biphenyl. Analysis was by mass spectrometry, with calibration by use of authentic samples.

EXAMPLE III 7.7 Grams (0.05 mole) of biphenyl were stirred and refluxed with 11.45 g. (0.05 mole) of silver benzoate for 2.5 hours at 230°–265° C. The cooled mixture was extracted with three 100 ml. portions of ether and the filtered ether solution was heated at a pot temperature of 220° C. at 200 mm Hg. to remove the ether. The 6.2 gram residue analyzed 50.2% biphenyl, 27.2% terphenyl, 19.0% quaterphenyl, and 3.6% quinquephenyl. Analysis was by mass spectrometry.

EXAMPLE IV 15.4 Grams (0.1 mole) of biphenyl were stirred and refluxed with 11.45 grams (0.05 mole) of silver benzoate at 245°–260° C. for 1.5 hours. The cooled residue was extracted with three 100 ml. portions of ether and the filtered ether solution was heated to a pot temperature of 250° C. at 200 mm Hg to remove the ether. The 4.5 gram residue analyzed 10.1% biphenyl, 22.3% terphenyl, 49.8% quaterphenyl, 12.9% quinquephenyl, and 4.9% sexiphenyl. Analysis was by mass spectrometry.

EXAMPLE V 3.8 Grams of triphenylphosphine complex of silver benzoate dissolved in 200 ml. of benzene were irradiated at 25° C. for 30 minutes by a 450 watt Hanovia lamp through a quartz well. Agitation was provided by a stream of nitrogen bubbling at 200 cc/minute through the solution. The solution darkened immediately, was black in 20 minutes. The benzene solution was filtered and distilled to remove the benzene. The 0.3 gram residue was 8% of the silver benzoate and consisted of 26.5% biphenyl, 6.2% terphenyl, 41.3% of phenyl biphenylyl phosphine (I)

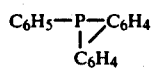  (I)

and 26.2% of diphenyl xenyl phosphine (II)

  (II)

Increased conversion of the silver benzoate resulted by irradiating the filtered benzene solution for another 20 minutes, filtering, and repeating. After 4 cycles the conversion was 28%. Analysis was by high-resolution mass spectrometry.

EXAMPLE VI 6.83 Grams (0.02 mole) of silver monomethyl terephthalate and 5.24 grams (0.02 mole) of triphenylphosphine were reacted by stirring in 250 ml of dry benzene. After one hour the triphenylphosphine complex of silver monomethyl terephthalate in benzene was filtered to remove the remaining insolubles. The solution was irradiated at 25° C. with a 450 watt Hanovia lamp for 30 minutes through quartz. The black silver metal was filtered from the solution and the benzene solution was heated to a pot temperature of 100° C. at 760 mm Hg to remove the benzene. The 0.287 gram residue represented 4.2% conversion of the silver monomethyl terephthalate and analyzed 48.8% methyl benzoate, 29.6% phenyl biphenylphosphine (formula I, Example V), 10.8% dimethyl biphenyl-4,4′-dicarboxylate (III),

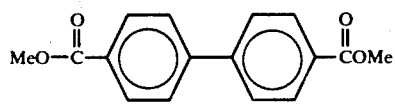  (III)

and 10.8% diphenyl (carbomethoxyl-biphenyl) phosphine (IV).

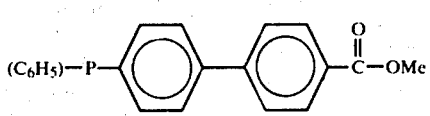  (IV)

Conversion of the triphenylphosphine complex of silver monomethylterephthalate could be increased by recycling the benzene solution after filtering from silver, which hampers light absorption. Analysis was by high-resolution mass spectrometry.

EXAMPLE VII 3.64 Grams (0.02 mole) of benzophenone were stirred and refluxed with 2.92 grams (0.01 mole) of silver benzoate under nitrogen at 300° C. for 30 minutes. The cooled mixture was extracted with three 100 ml. portions of benzene, and the filtered benzene solution was distilled at 100° C. and 0.2 mm Hg to remove the benzene and 1.95 grams of benzophenone. The 1.85 gram residue consisted of 16.5% biphenyl, 32.6% phenylbiphenyl ketone (V)

  (V)

14.3% di-biphenylketone (VI),

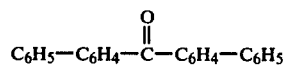  (VI)

and 36.6% dibenzoyl biphenyl (dimerized benzophenone) (VII). Analysis

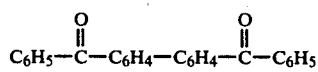  (VII)

was by mass spectrometry.

EXAMPLE VIII

Silver cinnamate, 5.1 grams, (0.02 mole) was heated in a Pyrex tube under nitrogen flowing at 50 cc/min. at 325° C. for 10 minutes. The distillate and the cooled mixture were taken up in ether. The filtered ether solution was heated on a steam bath to remove the ether. The residue analyzed 1.17 gram (56 mole % yield) of styrene and 0.28 grams of 1,4-diphenylbutadiene-1,3 (13.6 mole % yield). Analysis was by gas chromatography.

EXAMPLE IX

Silver o-chlorocinnamate, 5.8 grams (0.02 mole) was heated in a Pyrex tube at 295° C. for 10 minutes under nitrogen flowing at 50 cc/min. The distillate and the cooled mixture were dissolved in ether and filtered. The ether solution was heated on a steam bath to remove the ether. The residue was 1.77 grams of o-chlorostyrene, 64 mole % yield, and 0.17 grams of 1,4-di (o-chlorophenyl) butadiene-1,3 at 6.2 mole % yield. Analysis was by gas chromatography.

EXAMPLE X

Silver p-chlorocinnamate, 5.8 grams, (0.02 mole) was heated in a Pyrex tube at 350° C. for 15 minutes under a flow of nitrogen of 50 cc/min. The cooled residue was extracted with ether. The distillate was taken up in ether. The combined ether solutions were heated on a steam bath to remove the ether. The residue was 1.66 grams of p-chlorostyrene, 60 mole % yield, and 0.23 g of 1,4-(di-p-chlorophenyl) butadiene-1,3 at 8.3 mole % yield. Analysis was by gas chromatography.

EXAMPLE XI

Silver m-chlorocinnamate, 8.7 grams (0.03 mole) was heated in a Pyrex tube at 325° C. for 5 minutes under nitrogen flowing at 50 cc/min. The cooled residue was extracted with ether. The distillate was taken up in ether. The combined ether solutions were heated on a steam bath to remove the ether. The residue was 1.4 grams of m-chlorostyrene, 34 mole % yield, and 0.27 grams of 1,4-(di-m-chlorophenyl) butadiene-1,3 at 10 mole % yield. Analysis was by mass spectrometry.

EXAMPLE XII

Silver m-bromo-cinnamate, 10.2 grams, (0.03 mole) was heated in a Pyrex tube at 300° C. for 5 minutes under nitrogen flowing at 50 cc/min. The cooled residue was extracted with ether. The distillate was taken up in ether. The combined ether solutions were heated on a steam bath to remove the ether. The residue was 2.1 grams of m-bromostyrene, 38 mole % yield, and 0.2 g of 1.4-(di-m-bromophenyl) butadiene-1,3 at 4 mole % yield. Analysis was by mass spectrometry.

EXAMPLE XIII

Silver 2,4-dichlorocinnamate, 6.48 grams (0.02 mole) was heated in a Pyrex tube under nitrogen flowing at 50 cc/min at 300° C. for 10 minutes. The cooled residue was extracted with ether. The distillate was taken up in ether. The combined ether solutions were heated on a steam bath to remove the ether. The residue was 1.6 grams of 2,4-dichlorostyrene, 47 mole % yield, and 0.48 grams of 1,4-di(2,4-dichlorophenyl) butadiene-1,3 at 14 mole % yield. Analysis was by mass spectrometry.

EXAMPLE XIV

Silver 3,4-dichlorocinnamate, 6.48 grams (0.02 mole) was heated at 325° C. for 5 minutes in a Pyrex tube under nitrogen flowing at 50 cc/min. The cooled residue was extracted with ether. The distillate was taken up in ether. The combined ether solutions were heated on a steam bath to remove the ether. The residue was 2.7 grams of 3,4-dichlorostyrene (78 mole % yield) and 0.34 grams of 1,4-di(3,4-dichlorophenyl) butadiene-1,3 (10 mole % yield). Analysis was by mass spectrometry.

EXAMPLE XV

Finely-ground silver benzoate, 11.45 grams (0.05 mole) was heated in a sublimation apparatus at 0.3 Torr. At 270° C. the pressure in the system increased rapidly due to formation of $CO_2$ in the decarboxylation:

$$C_6H_5CO_2Ag \rightarrow C_6H_5 \cdot + CO_2 + Ag^\circ$$

Heating was continued at 310°–362° C. for 30 minutes. The sublimate and ether soluble extractables of the cooled residue weighed 2.38 grams after removal of the ether by heating on a steam bath. Benzene, 0.5 grams, was caught in the dry-ice trap. The other products, 2.3 grams, analyzed

| Product | Wt. % |
|---|---|
| Biphenyl | 28.8 |
| Terphenyl | 27.3 |
| Quaterphenyl | 10.6 |
| Quinquiphenyl | 2.2 |
| Sexiphenyl | 0.3 |
| Septaphenyl | 0.2 |

The insoluble residue, 6.5 grams, was silver metal and dissolved readily in warm 70% nitric acid. Analysis was by mass spectrometry.

EXAMPLE XVI

Silver m-toluate, 12.1 gram (0.05 mole) was heated slowly at atmospheric pressure under nitrogen flowing at 80 cc/min. At 275° C. 1.4 grams of toluene distilled. The temperature was raised to 400° C. and the flow of nitrogen increased to 200 cc/min. A yellow semi-solid distilled. It was taken up in ether. The ether solution was washed with aqueous sodium hydroxide, dried, and heated on a steam bath to remove the ether. The 1.1 gram residue analyzed 79% bitolyl and 5% tritolyl. Analysis was by mass spectrometry.

EXAMPLE XVII 7.68 Grams (0.04 mole) of trimellitic anhydride and 4.63 grams (0.02 mole) of silver oxide were mixed by being ground together, then were heated. At 180°–200° the black $Ag_2O$ became white as it formed monosilver trimellitate anhydride,

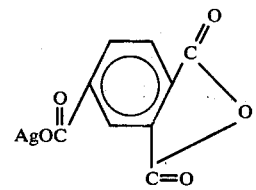

The silver salt was heated at 400° C. for 5 minutes, cooled, and extracted with acetone which was then removed by heating on a steam bath. The acetone residue plus sublimate from the decomposed silver salt weighed 2.2 grams. The product was 80% phthalic anhydride and 20% biphenyl tetracarboxylic acid dianhydride. Analysis was by mass spectrometry.

EXAMPLE XVIII

Potassium monomethyl terephthalate was prepared by adding dropwise a solution of 85.5 grams (1.286 mole) potassium hydroxide (85% pellets) in 675 ml methanol to a stirred solution of 250 grams (1.286 mole) of dimethyl terephthalate in 1600 ml. of benzene at 60° C. over 1 hour. The mixture was refluxed for 15 minutes, cooled, and filtered. The white solid on the filter was washed with acetone and sucked dry. It weighed 263 grams (93 mole % yield). It did not melt below 400° C.

A solution of 0.1 mole of silver nitrate in water was mixed with an aqueous solution of 21.8 grams (0.1 mole) of potassium monomethyl terephthalate. The precipitated silver monomethyl terephthalate was collected on a filter, washed, and dried. The 26.2 grams of silver salt, 82% mole % yield, decomposed at 370° C.

Silver monomethylterephthalate, 6.38 grams (0.02 mole) was heated at 400° C. for 15 minutes. The distillate was caught in a cooled receiver. The heated mixture was allowed to cool, and was extracted with acetone which was then removed by heating on a steam bath. The combined distillate and acetone extract residue weighed 2.2 gram. Analysis by gas chromatography indicated the products were:

| | |
|---|---|
| methyl benzoate | 17% |
| dimethyl terephthalate | 44% |

| | |
|---|---|
| 4-methyl biphenyl carboxylate | 13% |
| dimethyl biphenyl-4,4-dicarboxylate | 10% |

EXAMPLE XIX

Silver p-cyanobenzoate, which decomposed at 264° C., 11.6 grams (0.04 mole) was heated for 2 hours at 275°–325° C. under nitrogen at 50 cc/min. The benzene-soluble products, after driving off the benzene by heating the solution to dryness on a hot plate, weighed 3.3 grams and consisted of:

| | |
|---|---|
| benzonitrile | 42.5% |
| dicyanobenzene | 17.1% |
| cyanobiphenyl | 6.9% |
| dicyanobiphenyl | 6.5% |

Analysis was by mass spectrometry.

EXAMPLE XX

The silver salt of naphthalic acid, 1,8-naphthalene dicarboxylic acid, 3.2 grams (0.01 mole) was heated at 500° C. for 5 minutes. The cooled mixture was extracted with ether, acetone, and benzene. The solvents were evaporated by heating the solutions to dryness on a hot plate. By mass spectrometry, the 1.2 gram residue analyzed

| | |
|---|---|
| naphthalene | 36% |
| naphthalic anhydride | 25% |
| perylene | 3.6% |
| binaphthyl | 8% |
| naphthylnaphthalic anhydride | 6.3% |

EXAMPLE XXI

Silver 2-thiophene carboxylate 4.7 grams (0.02 mole) was heated at 300° C. for 5 minutes. The cooled mixture was extracted with ether. The ether was removed by heating on a steam bath. The 0.84 gram residue analyzed 61% thiophene and 21% bithienyl. Analysis was by gas chromatography.

EXAMPLE XXII 4.59 Grams (0.015 mole) of silver 4-biphenylcarboxylate were dried under nitrogen at 200° C. for 1 hour, then heated under nitrogen at 450° C. for one minute. The cooled mixture was extracted with benzene. The filtered benzene solution was evaporated to dryness on a hot plate. The 2.2 gram residue analyzed 19% biphenyl and 65% p-quaterphenyl. Analysis was by mass spectrometry.

EXAMPLE XXIII

8 Grams (0.0329 mole) of silver p-toluate were dried under nitrogen at 200° C. for one hour, then pyrolyzed under nitrogen at 400° C. for 2 minutes. The cooled mixture was extracted with ether. The filtered ether solution was evaporated to dryness on a steam bath. The 2.0 gram residue analyzed 21.1 wt. % 4,4'-dimethylbiphenyl. Analysis was by gas chromatography.

EXAMPLE XXIV 5.6 Grams (0.02 mole) silver 1-naphthoate (mp 230° dec.) were pyrolyzed under nitrogen at 250° C. for 5 minutes. The cooled mixture was extracted with benzene. The filtered benzene solution was evaporated to dryness on a hot plate. The 2 gram residue analyzed 49.0% naphthalene and 26.3% 1,1'-binaphthyl. Analysis was by gas chromatography.

EXAMPLE XXV 9.2 Grams (0.04 mole) of silver isonicotinate were pyrolyzed under nitrogen at 300°–350° C. for 2 minutes. The cooled products were extracted with boiling methanol. The filtered methanol solution was evaporated to dryness on a hot plate. The 1.2 gram of residue analyzed 75.6% 4,4'-bipyridyl and 13.3% terpyridyl. Analysis was by gas chromatography and mass spectrometry.

EXAMPLE XXVI 9.2 Grams (0.04 mole) of silver nicotinate were heated at 325°–350° C. for 2 minutes. The cooled mixture was extracted with hot methanol. The methanol solution was filtered and evaporated to dryness on a hot plate. The 2.0 gram residue analyzed 39.1% pyridine, 31.1% 3,3'-bipyridyl, and 12.6% terpyridyl. Analysis was by gas chromatography and mass spectrometry.

EXAMPLE XXVII 9.2 Grams (0.04 mole) of silver picolinate were heated at 325° C. for 2 minutes. The cooled mixture was extracted with hot methanol. The methanol solution was filtered and evaporated to dryness on a hot plate. The 3.6 gram residue analyzed 47.9% pyridine, 33.0% 2,2'-bipyridyl, and 7.6% terpyridyl. Analysis was by gas chromatography and mass spectrometry.

EXAMPLE XXVIII

The silver salt of o-fluorobenzoic acid, 4.94 gram, 0.02 mole, was pyrolyzed at 400° C. for 5 minutes. The cooled mixture was extracted with 200 ml of ether. The filtered ether solution was evaporated to dryness on a steam bath. The 0.6 gram residue analyzed 34.6% 2,2'-difluorobiphenyl, 26.4% trifluoroterphenyl, and 13.5% tetrafluoroquaterphenyl. Analysis was by gas chromatography and mass spectrometry.

EXAMPLE XXIX

The silver salt of m-fluorobenzoic acid, 9.88 gram (0.04 mole) was heated at 400° C. for 5 minutes. The cooled mixture was extracted with ether. The filtered ether solution was evaporated to dryness on a steam bath. The 1.8 gram residue analyzed 24.5%, 3,3'-difluorobiphenyl, 12.0% trifluoroterphenyl, and 4.2% tetrafluoroquaterphenyl. Analysis was by gas chromatography and mass spectrometry.

EXAMPLE XXX

The silver salt of p-fluorobenzoic acid, 9.88 gram (0.04 mole) was heated at 400° C. for 5 minutes. The cooled mixture was extracted with ether. The filtered ether solution was evaporated on a steam bath. The 2.3 gram residue analyzed 23.4% 4,4'-difluorobiphenyl, 11.8% trifluoroterphenyl, and 3.5% tetrafluoroquaterphenyl. Analysis was by gas chromatography and mass spectrometry.

EXAMPLE XXXI

The silver salt of pentafluorobenzoic acid, 6.38 grams (0.02 mole) was heated at 400° C. for 5 minutes. The cooled mixture was extracted with ether. The filtered ether solution was evaporated to dryness on a steam bath. The 1.5 gram residue analyzed 36.9% decafluorobiphenyl, 13.7% perfluoroterphenyl, and 5.9% perfluoroquaterphenyl. Analysis was by gas chromatography and mass spectrometry.

EXAMPLE XXXII

A mixture of 11.04 grams (0.05 mole) of silver trifluoroacetate and 9.11 grams (0.05 mole) of benzophenone was heated over one hour to 300° C. and kept at that temperature 45 minutes. The mixture was allowed to cool to room temperature. It was then extracted with three 200 ml portions of ether. The ether solution was filtered and then distilled using an electric heating mantle. 7.5 Grams of benzophenone and 1.75 grams of trifluoromethyl benzophenone isomers were recovered by distillation at 123°–125° C. and 0.3 Torr. Identification was by mass spectrometry. Conversion was 18%. Selectivity to trifluoromethyl benzophenone was 79%. The ether-insoluble product was 5.4 grams of silver metal.

EXAMPLE XXXIII

Silver trifluoroacetate is soluble in a wide variety of organic solvents, one of which is benzene. A solution of 11.05 grams (0.05 mole) of silver trifluoroacetate in 200 milliliters of benzene was pumped continuously through an Ace thin-film evaporator to expose a thin film to a high pressure mercury lamp through a quartz well. The solution was kept under nitrogen at 50 cc/minute at 22° C. for seven hours. A yield of 21 mole % of benzotrifluoride was obtained. Analysis was by gas chromatography.

A similar solution of 4.4 grams (0.02 mole) of silver trifluoroacetate in 600 ml of benzene was rotated in a one-liter quartz flask two inches from a 550 watt Hanovia high-pressure mercury lamp for six hours at 30° C. The irradiation was interrupted every two hours to remove the silver mirror that deposited on the flask surface with nitric acid. The filtered benzene solution was analyzed by gas chromotography. The yield of benzotrifluoride was 57 mole %.

EXAMPLE XXXIV 4.4 Grams (0.02 mole) of silver trifluoroacetate and 5.6 grams (0.02 mole) of 4-benzoylbiphenyl were heated at 300° C. for 10 minutes. The cooled mixture was extracted with benzene. The filtered benzene solution was distilled up to a pot temperature of 125° C. The 6.8 gram residue was analyzed by mass spectrometry. Conversion to trifluoromethylbenzoyl biphenyl was 17%. Selectivity was 81%.

EXAMPLE XXXV

A mixture of 4.4 grams (0.02 mole) of silver trifluoroacetate and 4.38 grams (0.02 mole) of coumarin was refluxed for ten minutes at 290° C. The cooled mixture was extracted with ether. The filtered ether solution was heated to dryness on a steam bath to remove the ether. The 6.7 gram residue was analyzed by mass spectrometry. Conversion of coumarin was 25.9% and selectivity to trifluoromethylcoumarin was 53%. Among other compounds formed were dicoumarylf, 29.5% selectivity, and trifluoromethyl dicoumaryl, 19.5% selectivity.

EXAMPLE XXXVI 11.04 Grams (0.05 mole) of silver trifluoroacetate and 10.3 ml (0.1 mole) of benzonitrile were heated in a bomb at 300° C. for 30 minutes. The cooled reaction mixture was extracted with ether. The filtered ether solution was heated to dryness on a steam bath to remove the ether. The residue was 9.06 grams of benzonitrile and 1.2 grams of trifluoromethylbenzonitrile, 70 mole % yield based on reacted benzonitrile. Analysis was by mass spectrometry.

What is claimed is:

1. A process for coupling compounds which comprises the steps of (1) reacting a monosilver salt compound having only one silver salt group per molecule selected from the group consisting of unsaturated, aliphatic carboxylic acids having 1 to 3 carbon-to-carbon double bonds and 3 to 26 carbon atoms, aromatic carboxylic acids, the aromatic groups of said aromatic carboxylic acids selected from the group consisting of phenyl, biphenyl, naphthyl, phenanthryl and anthranyl groups, and heterocyclic acids, the heterocyclic groups of said heterocyclic carboxylic acids being selected from the group consisting of thienyl, pyridyl, benzothienyl, thienobenzenyl, quinolyl, isoquinolyl, dibenzothienyl and phenanthridyl groups and mixtures thereof at a temperature within the range from about 100° to 500° C., (2) extracting the cooled mixture of silver and product with a solvent to recover the product by distillation or, alternatively, collecting the volatile products from the reactor in a cooled receiver and (3) recovering the silver metal.

2. The process of claim 1 wherein the said monosilver salt is reacted in the presence of a compound selected from the group consisting of aromatic compounds, the aromatic groups of said aromatic compounds being selected from the group consisting of phenyl, biphenyl, naphthyl, phenanthryl, anthranyl and benzophenone groups and heterocyclic compounds, the heterocyclic groups of said heterocyclic compounds being selected from the group consisting of thienyl, pyridyl, benzothienyl, thienobenzenyl, quinolyl, isoquinolyl, dibenzothienyl, and phenanthridyl groups, and mixtures thereof, the said aromatic compounds having a labile ring hydrogen and the said heterocyclic compound having a labile ring hydrogen.

3. The process of claim 1 wherein said monosilver salt is a silver salt of an $\alpha,\beta$-ethylenically unsaturated aliphatic carboxylic acid compound having 1 to 3 carbon-to-carbon double bonds and 3 to 26 carbon atoms.

4. The process of claim 3 wherein said monosilver salt of an $\alpha,\beta$-ethylenically unsaturated aliphatic carboxylic acid compound is selected from the group consisting of silver acrylate, silver sorbat, silver cinnamate and silver 1,3,5-heptatrieneoate compounds.

5. The process of claim 1 wherein said monosilver salt of an aromatic carboxylic acid is selected from the group consisting of silver benzoate, silver toluate, monosilver trimellitate anhydride, silver monomethyl terephthalate, silver para-cyanobenzoate, silver 1-naphthoate and silver 4-biphenyl carboxylate.

6. The process of claim 1 wherein said monosilver salt of a heterocyclic carboxylic acid is selected from the group consisting of silver 2-thiophene carboxylate, silver nicotinate, silver isonicotinate, and silver picolinate.

7. The process of claim 1 wherein said monosilver salt an aromatic carboxylic acid selected from the group consisting of silver benzoate, silver biphenyl carboxylate, silver 1-phenanthrene carboxylate, silver 2-phenanthrene carboxylate, silver 9-phenanthrene carboxylate, silver 1-anthracene carboxylate, silver 2-anthracene carboxylate, and silver 9-anthracene carboxylate.

8. The process of claim 2 wherein said monosilver salt is reacted in the presence of said compound and said compound is selected from the group consisting of quinoline, pyridine, biphenyl and benzophenone compounds.

9. The process of claim 2 wherein said monosilver salt is selected from the group consisting of silver 2-thiophene carboxylate, silver 2-pyridine carboxylate, silver 4-quinoline carboxylate, silver 1-isoquinoline carboxylate, silver 3-dibenzothiophene carboxylate, and silver 3-dibenzofuran carboxylate.

10. The process of claim 1 which consists essentially of the step of reacting the said monosilver salt of the said carboxylic acids wherein the said acids are polycarboxylic acids.

* * * * *

UNITED STATES PATENT AND TRADEMARK OFFICE
CERTIFICATE OF CORRECTION

PATENT NO. : 4,174,447
DATED : November 13, 1979
INVENTOR(S) : Ellis K. Fields

It is certified that error appears in the above—identified patent and that said Letters Patent is hereby corrected as shown below:

Column 1, line 17, "or benzoic acid" should read

-- of benzoic acid --.

Column 15, line 61, "dicoumarylf" should read

-- dicoumaryl --.

Column 16, line 49, "silver sorbat" should read

-- silver sorbate --.

Column 16, lines 61 and 62, "salt an" should read

-- salt is an --.

Signed and Sealed this

Twenty-fourth Day of June 1980

[SEAL]

Attest:

SIDNEY A. DIAMOND

Attesting Officer     Commissioner of Patents and Trademarks